US006706514B1

(12) United States Patent
Fournier et al.

(10) Patent No.: US 6,706,514 B1
(45) Date of Patent: Mar. 16, 2004

(54) POLYPEPTIDES CAPABLE OF INTERACTING WITH THE HUMAN TOPOISOMERASE IIIα

(75) Inventors: Alain Fournier, Chatenay-Malabry (FR); Hélène Goulaouic, Paris (FR); Jean-Francois Riou, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/856,930

(22) PCT Filed: Nov. 29, 1999

(86) PCT No.: PCT/FR99/02952

§ 371 (c)(1),
(2), (4) Date: Jun. 25, 2001

(87) PCT Pub. No.: WO00/32768

PCT Pub. Date: Jun. 8, 2000

(30) Foreign Application Priority Data

Nov. 30, 1998 (FR) ........................................... 98 15081

(51) Int. Cl.[7] ......................... C12N 9/90; C12N 15/00; C12N 21/04

(52) U.S. Cl. .................... 435/233; 435/183; 435/252.3; 435/320.1; 435/325; 536/23.1; 536/23.2; 536/23.5; 530/350; 530/358

(58) Field of Search .............................. 536/23.1, 23.2, 536/23.5; 435/183, 233, 320.1, 325, 252.3; 550/350, 358

(56) References Cited

FOREIGN PATENT DOCUMENTS

WO 984676 1/1998

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*

Confalonieri et al. Reverse gyrase: A helicase–like domain and a type I topoisomerase in the same polypeptide. Proc. Natl. Acad. Sci. USA 90:4753–4757 (1993).

Chung, J. et al. Identification of a Human Homolog of a Putative RNA Helicase Gene (mDEAD3) Expressed in Mouse Erythroid Cells. Korean J. Biochem. 27:193–197 (1995).

Ellis, N. et al. The Bloom's Syndrome Gene Product is Homologous to RecQ Helicases. Cell 83:655–666 (1995).

Forterre, P. et al. High Positive Supercoiling in vitro catalyzed by an ATP and polyethylene glycol–stimulated topoisomerase from *Sulfolobus acidocaldarius*. EMBO Journal 4(8):2123–2128 (1985).

Fritz, E. et al. Overexpression of a truncated human topoisomerase III partially corrects multiple aspects of the ataxia–telangiectasia phenotype. PNAS USA 94:4538–4542 (1997).

Gangloff, S. et al. The Yeast Type I Topoisomerase TOP3 Interacts with SGS1, a DNA Helicase Homolog: a Potential Eukaryotic Reverse Gyrase. Mol. and Cellular Biology 14(12):8391–8398 (1994).

Gee, S et al. Mouse erythroid cells express multiple putative RNA helicase genes exhibiting high sequence conservation from yeast to mammal. Gene 140:171–177 (1994).

Goulaouic, H. et al. Purification and Characterization of human DNA topoisomerase IIIα Nuc. Acid Res. 27(12):2443–2450 (1999).

Hanai et al. Human TOP3: A single–copy gene encoding DNA topoisomerase III. PNAS USA 93:3653–3657 (1996).

Lahn et al. Functional Coherence of the Human Y Chromosome. Science 278:765–680 (1997).

Li, W. et al. Mammalian DNA topoisomerase IIIα is essential in early embryogenesis. PNAS USA 95:1010–1013 (1998).

Mullen et al. Human homolgoues of yeast helicase. Nature 383:678–679 (1996).

Ng, S. et al. Anew human topoisomerase III that interacts with SGS1 protein. Nucl. Acids Res. 27(4):993–1000 (1999).

Rothstein & Gangloff Hyper–recombination and Bloom's Syndrome: Microbes Again Provide Clues about Cancer. Genome Research 5:421–426 (1995).

Seki, T. et al. Isolation of a cDNA encoding mouse DNA Topoisomerase III which is highly expressed at the mRNA level in the testis. Biochim. et Biophys. Acta 1396:127–131 (1998).

Wang, J. DNA Topoisomerases: Why so Many? J. Biol. Chem. 266(11):6659–6662 (1991).

* cited by examiner

*Primary Examiner*—Richard Hutson
(74) *Attorney, Agent, or Firm*—William C. Coppola

(57) ABSTRACT

The invention concerns novel polypeptides capable of interacting with the human topoisomerase IIIα and the nucleic acid sequences coding for said polypeptides. The invention also concerns a method for identifying compounds capable of interacting with said polypeptides and a method for identifying molecules capable of modulating the interaction of the topoisomerase IIIα with said polypeptides.

10 Claims, 1 Drawing Sheet

```
         BamHI       XhoI    Met Ala Leu Arg Gly Val Arg Lys Val Leu
   1     GGA TCC GAG CTC GAG ATG GCC CTC CGA GGC GTG CGG AAA GTC CTC
         CCT AGG CTC GAG CTC TAC CGG GAG GCT CCG CAC GCC TTT CAG GAG

         Cys Val Ala Glu Lys Asn Asp Ala Ala Lys Gly Ile Ala Asp Leu
  46     TGT GTG GCC GAA AAA AAC GAC GCG GCC AAG GGG ATC GCC GAC CTG
         ACA CAC CGG CTT TTT TTG CTG CGC CGG TTC CCC TAG CGG CTG GAC

---------------------------------------------------------------------

         Lys Cys Ser Leu Cys His Gln Pro Gly His Thr Arg Pro Phe Cys
2881     AAA TGC AGC CTT TGC CAC CAG CCT GGA CAC ACC CGT CCC TTT TGT
         TTT ACG TCG GAA ACG GTG GTC GGA CCT GTG TGG GCA GGG AAA ACA

         Pro Gln Asn Arg ***                         HindIII     Sal
2926     CCT CAG AAC AGA TGA GCT CAG GGT AGG GTA GAG AAG CTT GGA GTC
         GGA GTC TTG TCT ACT CGA GTC CCA TCC CAT CTC TTC GAA CCT CAG

         I
2971     GAC
         CTG
```

Figure 1

POLYPEPTIDES CAPABLE OF INTERACTING WITH THE HUMAN TOPOISOMERASE IIIα

The present invention relates to novel polypeptides capable of interacting with human topoisomerase IIIα and to the nucleic acid sequences encoding these polypeptides. It also relates, in addition, to a method for identifying compounds capable of interacting with said polypeptides and to a method for identifying molecules capable of modulating the interaction of topoisomerase IIIα with said polypeptides.

The replication of DNA is a complex mechanism which involves a large number of factors. DNA exists in the physiological state in a supercoiled form and access to the information which it contains requires substantial modification of the degree of coiling. Replication requires the suppression of the supercoils, the separation of the two strands of the DNA double helix and the maintaining of DNA in single-stranded form.

The modification of the degree of coiling is brought about in vivo by topoisomerases which are enzymes capable of modifying the DNA superstructures. It is possible to distinguish type I topoisomerases which cut only one of the two DNA strands and which eliminate the supercoils, and type II topoisomerases which act by cutting the two DNA strands and which are capable of eliminating or creating the supercoils. Eukaryotic topoisomerases are less well known than their prokaryotic homologs and their mechanism of action has still not yet been elucidated to date.

The separation of the two strands of a DNA duplex is catalyzed by a group of enzymes, called DNA helicases, which act in an ATP-dependent manner so as to produce the single-stranded DNA used as template for the DNA replication and transcription processes. Generally, the helicases bind to the single-stranded DNA or to the junctions between the single- and double-stranded DNA, and move in a single direction along the DNA in the double-stranded region, destroying the hydrogen bonds joining the two strands. All helicases exhibit a DNA-dependent ATPase (or. NTPase) activity which hydrolyzes the gamma phosphate of the ribonucleoside or deoxyribonucleoside 5'-triphosphate and provides the energy necessary for the reaction. The first helicase was discovered in *E. coli* in 1976. Since then, more than 60 helicases have been isolated in prokaryotes and eukaryotes. The role of human helicases has still not been elucidated in most cases, with the exception of HDHII (repair of the lesions induced by X-rays), HDHIV (assembly of preribosomes), ERCC2 and ERCC3, which are involved in repair through excision and cell viability. Little is known on the structure of these helicases. A large portion of the information available on the structures and functions of helicases has been obtained by comparative analysis of the amino acid sequences. In particular, conserved motifs have made it possible to group helicases into subfamilies based on the sequence homologies.

Human Topoisomerase III belongs to the family of type IA topoisomerases and therefore exhibits sequence homologies with *E. coli* topoisomerases I and III, yeast Topoisomerase III as well as reverse gyrase from archaebacteria. Human Topoisomerase III is now called Topoisomerase IIIα so as to differentiate it from human topoisomerase IIIβ which was recently discovered during the sequencing of the human immunoglobulin λ gene locus (Kawasaki, K., Minoshima, S., Nakato, E., Shibuya, K., Shintani, A., Schmeits, J. L., Wang, J. and Shimizu, N. 1997, Genome Research 7: 250–261), and for which no functional activity has been shown. Yeast-expressed and unpurified topoisomerase IIIα exhibits an activity of partial relaxation of a highly negatively supercoiled DNA (Hanai, R., Caron, P. R. and Wang, J. C. 1993. Proc. Natl. Acad. Sci. USA 93: 3653–3657).

Topoisomerase IIIα is a protein of 976 amino acids and with a molecular weight of about 110 kDa. The gene encoding human Topoisomerase IIIα is present in a single copy on chromosome 17p11.2–12 (Hanai, R., Caron, P. R. and Wang, J. C. 1996. Proc. Natl. Acad. Sci. USA 93: 3653–3657). A murine homolog of Topoisomerase III was recently cloned (Seki, T., Deki, M., Katada, T. and Enomoto, T. 1998. Biochim Biophys Acta 1396: 127–131).

Topoisomerase IIIα exhibits a strong sequence homology with yeast Topoisomerase III, namely 44% sequence identity and 61% similarity. The homology which it exhibits with bacterial topoisomerases I and III is less strong, namely 24% identity and 44% similarity. However, Topoisomerase IIIα resembles *E. coli* Topoisomerase I more than it resembles the other members of the group of type IA topoisomerases from the point of view of the organization of the protein into domains. Indeed, these two polypeptides contain a C-terminal domain which has no equivalent in *E. coli* or yeast Topoisomerase III. This C-terminal domain contains motifs with 4 cysteines (3 motifs for *E. coli* Topoisomerase I and 1.5 motif for human Topoisomerase IIIα), as well as an extreme C-terminal domain for which a DNA-binding role has been demonstrated for *E. coli* Topoisomerase I.

The role of human topoisomerase IIIα in the cell has not yet been identified.

Human Topoisomerase IIIα appears to be essential, at least during embryogenesis, since the knock-out of the murine homolog of Topoisomerase IIIα is lethal (Li, W. and Wang, J. C. 1998 Proc. Natl. Acad. Sci. USA 95: 1010–1013). The messenger RNAs for Topoisomerase IIIα are present in numerous tissues (heart, brain, placenta, lung, liver, skeletal muscle, kidney, pancreas) in the form of three transcripts of 7.2, 6 and 4 kilobases in size (Fritz, E., Elsea, S. H., Patel, P. I. and Meyn, M. S. 1997 Proc. Natl. Acad. Sci. USA 94: 4538–4542).

Moreover, it has been assumed that Topoisomerase IIIα plays a role in maintaining the stability of the genome. Indeed, the cDNA CAT4.5, encoding a truncated human Topoisomerase IIIα of 141 N-terminal amino acids, is capable of complementing the phenotype for hypersensitivity to ionizing radiation in AT (Ataxia-Telangectasia) cells exhibiting a mutation in the ATM gene (Fritz, E., Elsea, S. H., Patel, P. I. and Meyn, M. S. 1997 Proc. Natl. Acad. Sci. USA 94: 4538–4542).

In yeast, two independent studies have shown the existence of an interaction between the helicase SGS1 and yeast Topoisomerase III. On the one hand, the sgs1- mutants are suppressers of the top3- phenotype (slow growth, hyperrecombination) in the yeast *S. cerevisiae* (Gangloff, S., McDonald, J. P., Bendixen, C., Arthur, L. and Rothstein, R. 1994. Mol. Cell. Biol. 14: 8391–8398). On the other hand, it has been shown that the first 500 amino acids of SGS1 interact with yeast Topoisomerase III (Gangloff, S., McDonald, J. P., Bendixen, C., Arthur, L. and Rothstein, R. 1994. Mol. Cell. Biol. 14: 8391–8398, Lu, J., Mullen, J. R., Brill, S. J., Kleff, S., Romeo, A. M. and Sternglanz, R. 1996. Nature 383: 678–679). However, to date, no interaction between a helicase and human Topoisomerase IIIα has been identified.

The identification of partners of human topoisomerase IIIα therefore constitutes a major challenge for the understanding of the role of human topoisomerase IIIα, and of its mechanism of action.

The present invention results from the demonstration of novel polypeptides capable of interacting with topoisomerase IIIα (called hereinafter polypeptide partners of topoisomerase IIIα). It also results from the discovery that these polypeptides show a strong homology with proteins which exhibit structural characteristics common to RNA helicases and for which no function had so far been described. The demonstration of this interaction and of these homologies designate these proteins as DNA helicase partners of topoisomerase IIIα. The identification of these partners makes it possible to envisage numerous applications based on the combined action of these partner proteins and of topoisomerase IIIα; these applications relate in particular to:

1) The destruction of the nucleosomal structure: to undergo some processes such as replication, transcription, repair or recombination, DNA should be accessible to the corresponding enzymatic machineries and, to do this, the nucleosomal structure should be transiently destroyed. It is thus possible to envisage that helicase locally separates the DNA strands and creates positive supercoils ahead of it and negative supercoils behind it. The positive twist is absorbed by the disruption of the nucleosomes, while the negative twist is selectively relaxed by type IA topoisomerase.

2) The positive supercoiling of DNA: the interaction between helicase and type IA topoisomerase is likely to reconstitute in a eukaryotic organism the reverse gyrase activity of thermophilic archaebacteria. Indeed, it has been shown that *Sulfolobus acidocaldarius* reverse gyrase possesses at the N terminus a helicase domain containing the 8 motifs of helicases with a "DEAD" motif, and at the C terminus a topoisomerase domain homologous to the type IA topoisomerases (Confalonieri, F., Edie, C., Nadal, M., Bouthier de la Tour, C., Forterre, P. and Duguet, M. 1993. Proc. Natl. Acad. Sci. USA 90: 4753–4757); this enzyme relaxes the negatively supercoiled DNA and introduces positive supercoils into the circular DNA in an ATP-dependent manner (Forterre, P., Mirambeau, G., Jaxel, C., Nadal, M. and Duguet, M. 1985. EMBO J. 4: 2123–2128). This eukaryotic reverse gyrase activity can serve to eliminate particular DNA structures such as the cruciform DNA, the Z DNA, mismatches, recombination intermediates, and the like. From these observations and from the demonstration that topoisomerase IIIα is capable of interacting with a protein possessing the properties of a DNA helicase, it is possible to envisage the production in vivo or in vitro of a topoisomerase IIIα/protein partner complex constituting an enzymatic complex having reverse gyrase type functions. It should be noted that such a function of positive supercoiling of DNA has still never been described in eukaryotes.

3) The segregation of newly replicated chromosomes: at the end of the replication of DNA, topological problems appear at the level of the point of convergence of two replication forks. A mechanism which makes it possible to solve this topological problem involves the concerted action of a helicase and a type IA topoisomerase, capable of decatenating two single-stranded DNA molecules. This model (Wang, J. C. 1991. J. Biol. Chem. 266: 6659–6662; Rothstein, R. and Gangloff, S. 1995. Genome Research 5: 421–426) proposes that at the point where two replication forks meet, replication is stopped, leaving portions of entangled single-stranded DNAs. These are then separated by means of the concerted action of helicase and topoisomerase. The synthesis of DNA is then completed at the level of the single-stranded regions.

4) The recombination and the stability of the genome: it has been shown that mutants of Top3- yeast or Sgs1- mutants both exhibit a hyperrecombination phenotype while Top3-/Sgs1- double mutants recover a normal phenotype. This shows that yeast Topoisomerase III and helicase SGS1 probably act in a concerted manner to maintain a low rate of recombination, for example by a positive supercoiling activity of the reverse gyrase type, or by a more direct mechanism at the level of the pairings of the recombination intermediates.

Unlike the helicase SGS1, known to interact with yeast topoisomerase III, the protein partner of topoisomerase IIIα identified by the applicant does not belong to the family of RecQ type helicases.

The polypeptides according to the invention show a high degree of homology with the sequence of a human protein DDX14 published by Chung et al (Chung, J., Lee, S-G., and Song, K. 1995. Korean J. Biochem. 27: 193–197). The protein DDX14 exhibits a significant sequence homology with an RNA helicase of murine origin; however, the helicase activity of this protein has not yet been demonstrated and the function of DDX14 has not yet been elucidated.

The polypeptides according to the invention also show a high degree of homology with the sequence of a human protein DBX1 published by Lahn et al (Lahn, T. and Page, D. C. 1997. Science. 278: 675–680). The protein DBX1 encodes a protein which exhibits homologies with RNA helicases but its helicase activity has never been demonstrated and the function of the DBX1 protein has not yet been identified.

The DBX1 protein encodes a protein of 662 amino acids. The corresponding gene is situated on the X sex chromosome and its homolog situated on the Y chromosome is 91% identical at the protein level. The nucleic and polypeptide sequences of DBX1 are presented in the sequences SEQ ID No. 5 and SEQ ID No. 6. The expression of the DBX1 gene appears to be ubiquitous. It has now been demonstrated that the DBX1 protein possesses the 8 motifs characteristic of helicases of the "DEAD" family. More precisely, it belongs to the subfamily represented by the helicase PL10, and whose recorded members are the helicases DED1 and DBP1 from yeast, the helicase An3 from amphibians and the murine helicases PL10, mDEAD2 and mDEAD3 (Gee, S. L. and Conboy, J. G. 1994. Gene 140: 171–177). Helicases belonging to this subfamily contain, in addition to the central catalytic domain containing, the 8 conserved motifs of helicases, particular N- and C-terminal domains. The C-terminal domain is rich in arginines and serines, which resembles the domains of splicing factors. However, in the case of the helicases of this subfamily, this domain rich in arginines and serines is shorter and does not possess as many RS dipeptides as in the prototype domain of splicing factors.

The invention also provides a method for identifying molecules capable of blocking the interaction between human Topoisomerase IIIα and a polypeptide partner of topoisomerase IIIα. Such a method makes it possible to identify molecules which are in particular capable of blocking the reverse gyrase type activity of these two proteins. Such molecules are useful for modulating the processes of division, replication, transcription, translation, splicing, repair or recombination of DNA. These molecules are also capable of possessing a cytotoxic type antitumor activity because of the disruption of these basic processes at the level of the DNA.

A first subject of the invention therefore relates to nucleotide sequences encoding polypeptides capable of interacting with topoisomerase IIIα.

Preferably, the nucleotide sequences according to the invention encode a polypeptide comprising all or part of the polypeptide sequence described in the sequence SEQ ID No. 4 or its derivatives.

For the purposes of the present invention, the term derived polypeptide sequence denotes any polypeptide sequence differing from the sequence considered, obtained by one or more modifications of a genetic and/or chemical nature, and possessing the capacity to interact with topoisomerase IIIα. Modification of a genetic and/or chemical nature is understood to mean any mutation, substitution, deletion, addition and/or modification of one or more residues. Such derivatives may be generated with different aims, such as in particular that of improving its levels of production, that of increasing its resistance to proteases or of improving its passage across the cell membranes, that of increasing its therapeutic efficacy or of reducing its side effects, that of increasing the affinity of the peptide for its site of interaction, or that of conferring novel pharmacokinetic and/or biological properties on it. Advantageously, the variants comprise deletions or mutations affecting amino acids whose presence is not decisive for the activity of the derivative. Such amino acids may be identified for example by tests of cellular activity as described in the examples.

Preferably still, the nucleotide sequences according to the present invention comprise all or part of the nucleotide sequence described in the sequence SEQ ID No. 3 and encoding the sequence SEQ ID No. 4 or the sequences derived from this nucleotide sequence.

For the purposes of the present invention, the term derived nucleotide sequence denotes any sequence differing from the sequence considered because of the degeneracy of the genetic code, obtained by one or more modifications of a genetic and/or chemical nature, as well as any sequence hybridizing with these sequences or fragments thereof and encoding a polypeptide capable of interacting with Topoisomerase IIIα. The expression modification of a genetic and/or chemical nature is understood to mean any mutation, substitution, deletion, addition and/or modification of one or more residues. The term derivative also comprises the sequences homologous to the sequence considered, which are derived from other cellular sources and in particular from cells of human origin, or from other organisms. Such homologous sequences may be obtained by hybridization experiments. The hybridizations may be carried out starting with nucleic acid libraries, using the native sequence or a fragment thereof as probe, under variable hybridization conditions.

The nucleotide sequences according to the invention may be of artificial origin or otherwise. They may be genomic sequences, cDNA, RNA, hybrid sequences or synthetic or semisynthetic sequences. These sequences may be obtained for example by screening DNA libraries (cDNA library, genomic DNA library) by means of probes produced on the basis of sequences presented above. Such libraries may be prepared from cells of different origins by conventional molecular biology techniques known to persons skilled in the art. The nucleotide sequences of the invention may also be prepared by chemical synthesis or by mixed methods including chemical or enzymatic modification of sequences obtained by the screening of libraries. In general, the nucleic acids of the invention may be prepared according to any technique known to persons skilled in the art.

The subject of the present invention is also polypeptides capable of interacting with topoisomerase IIIα.

For the purposes of the present invention, the name topoisomerase IIIα covers human topoisomerase IIIα in itself as well as the homologous forms corresponding in particular to mutated forms of this protein.

Preferably, the polypeptides according to the invention comprise all or part of the polypeptide sequence described in SEQ ID No. 4 or of its derivatives.

The present invention also includes a polypeptide characterized in that it is a fragment of the DBX1 protein, capable of interacting with topoisomerase IIIα and comprising all or part polypeptide fragment which extends between residues 318–662 and represented in the polypeptide sequence SEQ ID No. 6 or its derivatives.

The subject of the present invention is also the use of the polypeptides according to the invention or of fragments of these polypeptides, for slowing down, inhibiting, stimulating or modulating the activity of topoisomerase IIIα.

Indeed, it is possible to envisage regulating the function of topoisomerase IIIα by means of the polypeptides according to the invention or of fragments thereof and in particular inhibiting or slowing down the activity of topoisomerase IIIα. This modification of the activity of topoisomerase IIIα is capable of leading to a slowing down of cellular growth or a blocking of the cell cycle or of inducing apoptosis.

Another subject of the present invention relates to a method for preparing the polypeptides according to the invention according to which a cell containing a nucleotide sequence encoding said polypeptides is cultured under conditions for expressing said sequence and the polypeptide produced is recovered. In this case, the part encoding said polypeptide is generally placed under the control of signals allowing its expression in a cellular host. The choice of these signals (promoters, terminators, leader sequence for secretion, and the like) may vary according to the cellular host used. Moreover, the nucleotide sequences of the invention may form part of a vector which may be autonomously replicating or integrative. More particularly, autonomously replicating vectors may be prepared using autonomously replicating sequences in the chosen host. As regards integrative vectors, these may be prepared, for example, using sequences homologous to certain regions of the genome of the host, allowing, through homologous recombination, the integration of the vector.

The subject of the present invention is also host cells transformed with a nucleic acid comprising a nucleotide sequence according to the invention. The cellular hosts which can be used for the production of the polypeptides of the invention by the recombinant route are both eukaryotic and prokaryotic hosts. Among the suitable eukaryotic hosts, animal cells, yeasts or fungi may be mentioned. In particular, as regards yeasts, yeasts of the genus Saccharomyces, Kluyveromyces, Pichia, Schwanniomyces or Hansenula may be mentioned. As regards animal cells, the insect cells Sf9, the cells COS, CHO, C127, of human neuroblastomas, and the like, may be mentioned. Among the fungi, Aspergillus ssp. or Trichoderma spp. may be more particularly mentioned. As prokaryotic hosts, the use of the following bacteria *E. coli*, Bacillus or Streptomyces is preferred.

According to a preferred mode, the host cells are advantageously represented by recombinant yeast strains.

Preferably, the host cells comprise at least one sequence or one fragment of a sequence chosen from the nucleotide sequences SEQ ID No. 3 or SEQ ID No. 5, for the production of the polypeptides according to the invention.

The nucleotide sequences according to the invention may be incorporated into viral or nonviral vectors, allowing their administration in vitro, in vivo or ex vivo.

Another subject of the invention relates, in addition, to any vector comprising a nucleotide sequence encoding a polypeptide according to the invention. The vector of the invention may be for example a plasmid, a cosmid or any DNA not encapsulated by a virus, a phage, an artificial chromosome, a recombinant virus, and the like. It is preferably a plasmid or a recombinant virus.

As viral vectors in accordance with the invention, there may be most particularly mentioned vectors of the adenovirus, retrovirus, adeno-associated virus, herpesvirus or vaccina virus type. The subject of the present application is also defective recombinant viruses comprising a heterologous nucleic sequence encoding a polypeptide according to the invention.

Another subject of the invention consists in polyclonal or monoclonal antibodies or antibody fragments directed against a polypeptide as defined above. Such antibodies may be generated by methods known to persons skilled in the art. In particular, these antibodies may be prepared by immunizing an animal against a polypeptide whose sequence is chosen from the sequences SEQ ID No. 4 or SEQ ID No. 6 or any fragment or derivative thereof, and then collecting blood and isolating antibodies. These antibodies may also be generated by preparing hybridomas according to techniques known to persons skilled in the art. The antibodies or antibody fragments according to the invention may in particular be used to inhibit and/or reveal the interaction between topoisomerase IIIα and the polypeptides as defined above.

Another subject of the present invention relates to a method for identifying compounds capable of binding to the polypeptides according to the invention. The identification and/or isolation of these compounds or ligands may be carried out according to the following steps:

- a molecule or a mixture containing various molecules, optionally unidentified, is brought into contact with a polypeptide of the invention under conditions allowing the interaction between said polypeptide and said molecule in the case where the latter might possess affinity for said polypeptide, and,
- the molecules bound to said polypeptide of the invention are detected and/or isolated.

According to a particular mode, such a method makes it possible to identify molecules capable of blocking the helicase type activity, in particular the DNA helicase activity of the DBX1 protein or of the polypeptides according to the invention and thus modulate the processes of division, replication or transcription of DNA. These molecules are capable of possessing a cytotoxic type antitumor activity because of the disruption of these basic processes at the level of the DNA.

In this regard, another subject of the invention relates to compounds or ligands capable of binding to the polypeptides according to the invention and capable of being obtained according to the method defined above.

Another subject of the invention relates to the use of a compound or of a ligand identified and/or obtained according to the method described above as a medicament. Such compounds are indeed capable of being used for the prevention, improvement or treatment of certain conditions involving a cell cycle dysfunction.

The subject of the invention is also any pharmaceutical composition comprising, as active ingredient, at least one ligand obtained according to the method described above.

Another subject of the present invention relates to a method of identifying compounds capable of modulating or of completely or partially inhibiting the interaction between topoisomerase IIIα and the polypeptides according to the invention or the DBX1 protein.

The identification and/or isolation of modulators or ligands capable of modulating or of completely or partially inhibiting the interaction between topoisomerase IIIα and the polypeptides according to the invention or the DBX1 protein may be carried out according to the following steps:

- the binding of topoisomerase IIIα or of a fragment thereof to a polypeptide according to the invention is carried out;
- a compound to be tested for its capacity to inhibit the binding between topoisomerase IIIα and the polypeptides according to the invention is added;
- it is determined whether topoisomerase IIIα or the polypeptides according to the invention are displaced from the binding or prevented from binding;
- the compounds which prevent or which impede the binding between topoisomerase IIIα and the polypeptides according to the invention are detected and/or isolated.

In a particular mode, this method of the invention is suited to the identification and/or isolation of agonists and antagonists of the interaction between topoisomerase IIIα and the polypeptides of the invention. Still according to a particular mode, the invention provides a method for identifying molecules capable of blocking the interaction between human Topoisomerase IIIα and the helicase DBX1.

Such a method makes it possible to identify molecules capable of blocking the reverse gyrase type activity of these two proteins and thus modulate the processes of division, replication, transcription, translation, splicing, repair or recombination of DNA. These molecules are capable of possessing a cytotoxic type antitumor activity because of the disruption of these basic processes at the level of the DNA.

In this regard, another subject of the invention relates to compounds or ligands capable of interfering at the level of the interaction between topoisomerase IIIα and the polypeptides according to the invention or the DBX1 protein and which are capable of being obtained according to the method defined above.

The invention also relates to the use of a compound or of a ligand identified and/or obtained according to the method described above as a medicament. Such compounds are indeed capable of being used for the prevention, improvement or treatment of certain conditions involving a cell cycle dysfunction.

The subject of the invention is also any pharmaceutical composition comprising, as active ingredient, at least one ligand obtained according to the method described above.

Other advantages of the present invention will emerge from reading the examples which follow and which should be considered as illustrative and nonlimiting.

LEGEND TO THE FIGURES

FIG. 1: This figure represents the beginning and the end of the sequence SEQ ID No. 1 so as to present the introduction of the BamHI and SalI sites in 5' and 3' of the topoisomerase IIIα coding sequence and the position of the XhoI and HindIII sites.

MATERIALS AND METHODS

1) General Molecular Biology Techniques

The methods conventionally used in molecular biology such as preparative extractions of plasmid DNA, centrifugation of plasmid DNA in cesium chloride gradient, electrophoresis on agarose or acrylamide gels, purification of DNA fragments by electroelution, phenol or phenol-chloroform extractions of proteins, precipitation of DNA in saline medium with ethanol or isopropanol, transformation in Escherichia coli, and the like, are well known to persons skilled in the art and are abundantly described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

For the ligations, the DNA fragments may be separated according to their size by electrophoresis on agarose or acrylamide gels, extracted with phenol or with a phenol/chloroform mixture, precipitated with ethanol and then incubated in the presence of T4 phage DNA ligase (Biolabs) according to the supplier's recommendations.

The filling of the protruding 5' ends may be carried out with the Klenow fragment of *E. coli* DNA Polymerase I (Biolabs) according to the supplier's specifications. The destruction of the protruding 3' ends is carried out in the presence of the T4 phage DNA Polymerase (Biolabs) used according to the manufacturer's recommendations. The destruction of the protruding 5' ends is carried out by a controlled treatment with S1 nuclease.

Mutagenesis directed in vitro by synthetic oligodeoxynucleotides may be carried out according to the method developed by Taylor et al. [Nucleic Acids Res. 13 (1985) 8749–8764] using the kit distributed by Amersham.

Enzymatic amplification of DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350] may be carried out using a "DNA thermal cycler" (Perkin Elmer Cetus) according to the manufacturer's specifications.

The verification of the nucleotide sequences may be carried out by the method developed by Sanger et al. [Proc. Natl. Acad. Sci. USA, 74 (1977) 5463–5467] using the kit distributed by Amersham.

2) The Yeast Strains Used are

The strain yCM17 of the genus *S. cerevisiae* (MATa, ura3-52, his3-200, ade2-101, lys2-801, trp1-901, leu2-3, 112, canr, gal4-542, gal80-538, URA3::GAL1/10-lacZ-URA3) was used as tool for screening the library for fusion of Hela cells by the two-hybrid system.

The strain L40 of the genus *S. cerevisiae* (MATa, his3D200, trpl-901, leu2-3,112, ade2, LYS2::(lexAop)4-HIS3, URA3:(lexAop)8-LacZ, GAL4) was used to verify the protein-protein interactions when one of the protein partners is fused with the LexA protein. The latter is capable of recognizing the LexA response element controlling the expression of the LacZ and His3 reporter genes.

They were cultured on the following culture media:

Complete YPD medium: yeast extract (10 g/l) (Difco), bactopeptone (20 g/l) (Difco), glucose (20 g/l) (Merck). This medium was made solid by addition of 20 g/l of agar (Difco).

Minimum YNB medium: Yeast Nitrogen Base (without amino acids) (6.7 g/l) (Difco), glucose (20 g/l) (Merck). This medium may be made solid by addition of 20 g/l of agar (Difco). This medium is supplemented with amino acids or nitrogen bases (50 mg/ml) which are necessary to bring about the growth of auxotrophic yeasts. Ampicillin (100 $\mu$g/ml) is added to the medium so as to avoid bacterial contaminations.

3) The Bacterial Strains Used are

The *Escherichia coli* TG1 strain of the supE, hsd$\Delta$5, thi, $\Delta$(lac-proAB), F'[tra D36 pro $A^+B^+$ $lacI^q$ lacZ$\Delta$M15] genotype was used for the construction of the plasmids pLex-TopoIII$\alpha$ and pGBT-TopoIII$\alpha$.

The *Escherichia coli* HB101 strain of the supE44, ara14, galK2, lacY1, $\Delta$(gpt-proA)62, rpsL20($Str^r$), xyl-5, recA13, $\Delta$(mcrC-mrr), $HsdS^-(r^-m^-)$ gentotype was used as means for amplifying and isolating plasmids obtained from the Hela cell cDNA library.

The TG1 strain was cultured on LB medium: NaCl (5 g/l) (Difco), bactotryptone (10 g/l) (Difco), yeast extract (5 g/l) (Difco). This medium may be made solid by adding 20 g/l of agar (Difco). Ampicillin was used at 100 $\mu$g/l for the selection of bacteria which have received plasmids carrying, as marker, the gene for resistance to this antibiotic.

The HB101 strain was cultured on M9 medium: Na2HPO4 (7 g/l) (Sigma), KH2PO4 (3 g/l) (Sigma), NH4Cl (1 g/l) (Sigma), NaCl (0.5 g/l) (Sigma), glucose (20 g/l) (Sigma), MgSO4 (1 mm) (Sigma), thiamine (0.001%). This medium is made solid by adding 15 g/l of agar (Difco).

Leucine (50 mg/l) (Sigma) and proline (50 mg/l) (Sigma) are added to the M9 medium to allow growth of the HB101 strain. During the selection of plasmids obtained from the Hela cell two-hybrid cDNA library, leucine was not added to the medium because the plasmids carry a Leu2 selection marker.

3) The Plasmids Used are

Vector pGBT9 (+2): this plasmid is derived from the plasmid pGBT9 (Clontech). It exhibits a reading frame shift of +2, upstream of the EcoR1 site, in the zone corresponding to the multiple cloning site. The difference in sequence between pGBT9 (+2) and pGBT9, upstream of the EcoRI site (underlined), is represented in bold below:

SEQ ID No. 7 pGBT9 (+2):

TCG CCG GAA TTG AAT TCC CGG GGA TCC GT

SEQ ID No. 8 pGBT9:

TCG CCG GAA TTC CCG GGG ATC CGT

The vector PGBT9 (+2) is a shuttle plasmid of 5.4 kb which possesses a bacterial and yeast replication origin allowing it to replicate in a high copy number in these two microorganisms. This plasmid contains a multiple cloning site situated downstream of the sequence encoding the DNA-binding domain of GAL4 and upstream of a terminator to form a fusion protein. It also contains the *S. cerevisiae* TRP1 gene which makes it possible to complement yeasts of the trp1 genotype so as to select them on a minimum medium not containing tryptophan. This vector carries the gene for resistance to ampicillin which makes it possible to select the bacteria on a medium containing ampicillin.

pGBT-HaRasVal12: plasmid derived from pGBT9 and comprising the sequence encoding the HaRas protein mutated at position Val12 known to interact with the mammalian Raf protein. This plasmid was used to test the specificity of interaction of the protein according to the invention with human topoisomerase III$\alpha$.

PGBT-Fe65: plasmid derived from pGBT9 and comprising a portion of the sequence encoding the Fe65 protein known to interact with the cytoplamic region of APP (Amyloid Peptide Precursor). This plasmid was used as a control to verify the specificity of interaction of the protein according to the invention with human topoisomerase III$\alpha$ The vector pGAD GH: provided by Clontech and which allows the expression in yeast of proteins from the fusion between the transactivating domain of GAL4 and a protein encoded by the cDNA obtained from a Hela cell library, inserted at the level of the EcoRI and XhoI sites.

The vector pLex9 (pBTM116) (Bartel et al D. A. Hartley Ed, Oxford University press page 153) of 5 kb homologous to pGBT10 which contains a multiple cloning site downstream of the sequence encoding the bacterial LexA repressor and upstream of a terminator to form a fusion protein.

4) The Synthetic Oligonucleotides Used are

SEQ ID No. 9 oligonucleotide 124
CGAGGTCTGAGGATGATCTT

SEQ ID No. 10 oligonucleotide 125
CTGAGAAAGTGGCGTTCTCT

This pair of oligonucleotides served to amplify by PCR, starting with a Hela cell cDNA library, a fragment corresponding to the sequence encoding human topoisomerase IIIα.

SEQ ID No. 11 oligonucleotide Top3Xho1
AAGTTACTCGAGATGGCCCTCCGAGG

SEQ ID No. 12: oligonucleotide Top3Hind3
ACGAGCAAGCTTCTCTACCCTACCCTG

The pair of oligonucleotides Top3Xho1 and Top3Hind3 made it possible to introduce the XhoI and HindIII sites respectively during a second PCR step on the fragment corresponding to topoisomeraseIIIα previously amplified by means of oligonucleotides 124 and 125.

SEQ ID No. 13: oligonucleotide PCS1
AATTGCGAATTCTCGAGCCCGGGGATC-CGTCGACTGCA

SEQ ID No. 14: oligonucleotide PCS2
GTCGCAGGATCCCCGGGCTCGAGAATTCGC

The pair of oligonucleotides PCS1 and PCS2 made it possible to introduce to the plasmid pLex9 a XhoI site in phase with the human topoisomeraseIIIα coding sequence. The insert comprising the gene encoding topoisomerase IIIα was therefore recloned into this vector between the sites XhoI in 5' and Sal I in 3'.

SEQ ID No. 15 oligonucleotide GAL4TA
CCACTACAATGGATGATG

This oligonucleotide was used to sequence the inserts contained in the plasmids of the Hela cell two-hybrid cDNA library.

The oligonucleotides are synthesized on the Applied System ABI 394-08 apparatus. They are detached from the synthesis template with ammonia and precipitated twice with 10 volumes of n-butanol and then taken up in water. The quantification is carried out by measuring the optical density (one OD unit corresponds to 30 μg/ml).

5) Transformation of the TG1 Bacteria

The entire ligation volume (10 μl) is used to transform the TG1 bacteria made competent by the Chung et al. method (PNAS, 1988 86, 2172–2175).

The TG1 bacteria are cultured in a liquid LB medium for a few hours in a shaking incubator at 37° C., until an OD of 0.6 to 600 nm is obtained. The medium is then centrifuged at 6000 rpm for 10 min. The bacteria are made competent by taking up the bacterial pellet in a volume of TSB (LB medium+100 g/l of PEG 4000, 5% of DMSO, 10 mM $MgCl_2$, 10 mM $MgSO_4$) corresponding to 1/10 of the volume of the initial culture medium. After incubation at 4° C. for 30 to 60 minutes, 200 μl of bacteria are brought into contact with the ligation products for 15 minutes on ice. After addition of 200 μl of LB, the bacteria are incubated for 30 min at 37° C. and then plated on an LB+ampicillin medium.

6) Preparation of Plasmids From the Hela Cell two-Hybrid cDNA Library (Clontech®)

The Hela cell two-hybrid cDNA library is sold in the form of bacteria. The latter contain a plasmid PGAD GH containing an insert corresponding to a Hela cell cDNA. The cDNAs of this library are constituted by means of an oligodT primer. These cDNAs are cloned in an orientated manner into the vector pGAD GH at the level of the EcoRI and XhoI. 2.1 sites)

The plasmid DNA of the brain cDNA library was extracted according to the Clontech® protocol. To preserve the representativeness of the library which consists of 1.2×$10^6$ independent plasmids, the batch of plasmid DNA was prepared from a number of isolated bacterial colonies corresponding to a little over twice the representativeness of the library, that is 4×$10^6$ colonies.

After verification of the titre of the library, 2 μl of bacteria of the Hela cell two-hybrid cDNA library, previously placed in 8 ml of LB, are plated on a solid medium (16 dishes/770 $cm^2$ in LB+ampicillin medium). The colonies which appear are taken up for each of the dishes in 30 ml of liquid LB+ampicillin. The suspensions obtained are incubated at 37° C. for 3 hours. The DNA is then extracted from these strains by the technique for extracting plasmid DNA in a large quantity. The DNA concentration is determined at 260 nm.

7) Transformation of Yeast

The yeasts previously cultured in 100 ml of liquid medium are harvested by centrifugation (3000 rpm, 3 minutes). The pellet is washed twice by centrifuging with 1 ml of sterile water. The yeasts are then taken up in 1 ml of transformation solution I (0.1 M LiAc, 10 mM Tris-HCl pH 7.5, 1 mM EDTA) and then centrifuged (3000 rpm, 3 minutes). The pellet is taken up in 1 ml of transformation solution I. 50 μl of this yeast suspension are brought into contact with 50 μg of salmon sperm DNA and 1 to 5 μg of plasmid DNA and 300 μl of a transformation solution II (0.1 M LiAc, 10 mM Tris-HCl pH 7.5, 1 mM EDTA in 40% $PEG_{4000}$). This mixture is incubated at 28° C. for 30 minutes. After application of a heat shock (40° C., 15 minutes), the cells are harvested by centrifugation (15000 rpm for 1 min). This pellet is taken up in 200 μl of water and then plated on a minimum agar medium not containing amino acids corresponding to the resistance markers carried by the plasmids transforming the yeasts. The yeasts are incubated for 72 hours at 28° C.

8) Transformation of Yeast With the Hela Cell two-Hybrid cDNA Library

The yeast used was transformed beforehand with the plasmid pLexTopoIIIα. It is cultured in minimum YNB+His+Lys+Ad+Leu medium (250 ml), at 28° C., with stirring until a density of $10^7$ cells/ml is obtained. The cells are harvested by centrifugation (3000 rpm, 10 minutes) and then taken up in 250 ml of water. After another centrifugation, the cellular pellet is taken up in 100 ml of water and again centrifuged. The pellet is then taken up in 10 ml of transformation solution I and incubated for 1 hour at 28° C. with stirring. After centrifugation, the cells are again taken up in 2.5 ml of transformation solution I, 100 μl of the Hela cell cDNA library and 20 ml of transformation solution II, and then incubated for 1 hour at 28° C. with stirring. A heat shock is applied to this transformation mixture at 42° C. for 20 minutes. The cells are then centrifuged and the cellular pellet harvested is washed with 10 ml of sterile water. This operation is repeated twice and then the pellet is taken up in 2.5 ml of PBS. At this stage, the PEG which is toxic to the cells is removed. 2.4 ml of this suspension are used to inoculate 250 ml of minimum medium containing the amino acids His, Lys, Ad and cultured overnight in a shaker at 28° C. The remaining 100 μl of this suspension serve to determine the transformation efficiency by dilution on solid minimum medium in the presence of His, Lys and Ad. The overnight culture is then centrifuged (3000 rpm for 5 min) and washed twice with sterile water. The pellet is then taken up in 2.5 ml of water. One aliquot of 2.4 ml of this mixture is brought to 10 ml in sterile water, this solution is used to inoculate 10 dishes of 435 $cm^2$ containing 200 ml of YNB+Lys+Ad medium and incubated for 3 days. The remaining 100 μl are used to determine the level of amplification of the number of colonies during an overnight culture.

9) Extraction of Nucleic Acids From Yeasts

The value of an average loop of a yeast clone is placed in 200 μl of a TELT solution (2% Triton X100, 1% SDS, 100 mM NaCl, 10 mM Tris pH 8, 1 mM EDTA), in the presence of 3 g of glass beads 450 μm in diameter and 200 μl of phenol/chloroform. This mixture is stirred for 15 minutes and then centrifuged for 2 minutes at 14000 rpm. The supernatant is collected without removing the protein cake and the DNA contained in this phase is precipitated with 2.5 volumes of absolute ethanol. After centrifuging for 2 minutes at 14000 rpm, the DNA pellet is dried and taken up in 20 μl of TE-RNAse. 3 μl of this DNA solution previously dialyzed against water, which corresponds to a mixture of nucleic acids, serves directly to transform HB101 bacteria. Only the plasmid DNA is capable of replicating in the bacteria and may be analyzed by the technique for preparing plasmid DNA from bacteria in a small quantity.

10) Test for β-galactosidase Activity

A nitrocellulose sheet is deposited beforehand on the Petri dish containing the individualized yeast clones. This sheet is then immersed in liquid nitrogen for 30 seconds so as to break the yeasts and thus release the β-galactosidase activity. After thawing, the nitrocellulose sheet is deposited, colonies at the top, in another Petri dish containing a Whatman 3M paper impregnated beforehand with 1.5 ml of PBS solution (60 mM $Na_2HPO4$, 40 mM $NaH_2PO_4$, 10 mM KCl, 1 mM $MgSO_4$, pH 7) and 10 to 30 μl of X-Gal (5-bromo-4-chloro-3-indoyl-β-D-galactoside) containing 50 mg/ml of N,N-dimethylformamide. The dish is then incubated at 37° C.

EXAMPLE 1

Construction of a Vector Allowing the Expression of a Protein From the Fusion Between Human Topoisomerase IIIα and a DNA-binding Protein The screening of a cDNA library using the two-hybrid system requires beforehand that the human topoisomerase IIIα is fused with a protein capable of binding to the promoters controlling the expression of reporter genes such as the LexA protein of the bacterial repressor or the DNA-binding domain (DB) of GAL4. The expression of the fusion proteins is carried out by means of the vector pLex9 in the case of a fusion with the LexA protein or by means of the vector pGBT9 (+2) for a fusion with the DB of GAL4 (cf. Materials and Methods). The sequence encoding the human topoisomerase IIIα presented in SEQ ID No. 1 was introduced into these two types of vector in the same reading frame as the sequence corresponding to the LexA protein or to the DB of Gal4.

The DNA fragment corresponding to the sequence encoding human topoisomerase IIIα was amplified by PCR from a Hela cell cDNA library (Clontech) by means of oligonucleotides 124 and 125. A second PCR amplification step was performed on the DNA fragment so as to introduce at the two ends the XhoI and HindIII sites by means of the pair of oligonucleotides Top3Xho1 and Top3Hind3. The new DNA fragment obtained, digested with XhoI and HindIII, was introduced at the corresponding sites into the vector pBlueBacHis2A (Invitrogen) which gives the possibility of using new BamHI and SalI restriction sites (represented in bold with the XhoI and HindIII sites in FIG. 1) so as to produce the final constructs.

The plasmid pLex-TopoIIIα was constructed by inserting the XhoI-SalI fragment, of the preceding plasmid, corresponding to human topoisomeraseIIIα, into the plasmid pLex9 modified beforehand by insertion of the oligonucleotides PCS1 and PCS2 at the EcoRI-PstI1 sites. This plasmid was used to screen a Hela cell two-hybrid cDNA library with the aim of identifying proteins interacting with human topoisomerase IIIα.

The plasmid pGBT-TopoIIIα was constructed by inserting, at the BamHI and SalI sites of the plasmid pGBT9 (+2), a fragment obtained by partial digestion with BamHI and total digestion with SalI and corresponding to human topoisomerase IIIα. This plasmid was used to validate, by the two-hybrid technique, the specificity of interaction of the proteins selected during the screening with human topoisomerase IIIα.

The constructs were verified by sequencing the DNA. This verification made it possible to show that the fragments of human topoisomerase IIIα did not exhibit mutations generated during the PCR reaction and that they were fused in the same open reading frame as that of the fragments corresponding to the LexA protein or to the DB of GAL4.

EXAMPLE 2

Screening by the two-Hybrid Technique of a HeLa Cell cDNA Library

The screening of a fusion library makes it possible to identify clones producing proteins fused with the transactivating domain of GAL4, which can interact with topoisomerase IIIα. This interaction makes it possible to reconstitute a transactivator which will then be capable of inducing the expression of the reporter genes His3 and LacZ in the L40 strain used.

To carry out this screening, a fusion library produced from cDNA obtained from Hela cells was chosen.

Transformation of Yeast With the Hela Cell two-Hybrid cDNA Library and Selection of the Positive Clones During the screening, it is necessary to preserve the probability that each independent plasmid of the fusion library is present in at least one yeast at the same time as the plasmid pLex-TopoIIIα. To preserve this probability, it is important to have a good efficiency of transformation of the yeast; for this purpose, a yeast transformation protocol giving an efficiency of $10^5$ transformed cells per μg of DNA was chosen. Furthermore, as the cotransformation of yeast with two different plasmids reduces this efficiency, an L40 yeast transformed beforehand with the plasmid pLex-TopoIIIα was used. This strain containing pLex-TopoIIIα, of the phenotype His-, Lys-, Leu-, was transformed with 100 μg of plasmid DNA the two-hybrid library. This quantity of DNA made it possible to obtain after estimation (see Materials and Methods) $6\times10^6$ transformed cells, which corresponds to the number of independent plasmids which the library constitutes. It is thus possible to estimate that less than all of the plasmids of the library served to transform the yeasts. The selection of the transformed cells, capable of reconstituting a functional GAL4 transactivator, was performed on an YNB+Lys+Ad medium.

At the end of this selection, about 500 clones of the His+ phenotype were obtained. A test for β-galactosidase activity was performed on these transformants so as to determine the number of clones expressing the other reporter gene, LacZ. Of the 500 clones obtained, sixty-three exhibited the double phenotype His+ and βGal+, thus showing that they express proteins which can interact with human topoisomerase IIIα.

EXAMPLE 3

Isolation of the Plasmids From the Yeast Clones Selected

To identify the proteins which interact with human topoisomerase IIIα, the plasmids obtained from the two-hybrid library of the yeasts selected during the two-hybrid screening were extracted. The DNA of the yeast strains of the phenotype His+ and βGal+ is used to transform the *E. coli* HB101 strain.

The plasmid DNAs of the bacterial colonies obtained after transformation with yeast DNA extracts were analyzed by digesting with restriction enzymes and separating the DNA fragments on agarose gel. Two different restriction profiles were obtained out of 15 yeast clones analyzed. One of these profiles was highly represented. These results show that at least 2 different plasmids were isolated during this screening, the DNA fragment obtained from the cDNA library contained in the most highly represented plasmid was selected for the remainder of the study.

EXAMPLE 4

Determination of the Sequence of the Insert Contained in the Plasmid Selected The sequencing was carried out on the most highly represented plasmid. The sequencing is carried out using the oligonucleotide GAL4TA complementary to the region close to the site of insertion of the Hela cell cDNA library, at 52 base pairs from the EcoRI site.

Comparison of the sequence obtained with the sequences contained in the GenBank and EMBL (European Molecular Biology Lab) databanks has shown that the sequence of the cDNA present in the plasmid selected exhibits 98.2% at the nucleic level with the human gene encoding the Dead Box X isoform protein (DBX1) also called helicase like protein 2 (DDX14) having the accession number AF000982 and U50553 respectively. Comparison of the sequence of the cDNA present in the plasmid selected also shows 98.1% identity with the DDX14 protein.

The nucleotide and polypeptide sequence of DBX1 is presented in the sequence SEQ ID No. 5. The sequence of the gene cloned by two hybrids starts at nucleotide 952 relative to the putative initiation codon, that is at the 318th amino acid and contains a sequence homologous to the sequence encoding the C-terminal part of the DBX1 protein including the stop codon.

This result shows that the domain for interaction of the protein or polypeptide partners of human topoisomerase IIIα is contained in the second C-terminal half of said partners.

Differences were noted relative to the published DBX1 sequence, in particular the AGT codon (at position 1768 relative to the initiation codon, that is at position 2624 on the sequence SEQ ID No. 5) encoding serine 590 is absent in the cloned fragment.

Likewise, the presence of a C residue in place of a T at position 2068 of the ATG was noted.

The sequence of the cloned fragment is represented in SEQ ID No. 3.

EXAMPLE 5

Analysis of the Specificity of Interaction Between Topoisomerase IIIα and the Polypeptides of the Invention The specificity of interaction between human topoisomerase IIIα and the polypeptide according to the invention was confirmed in a two-hybrid interaction test using the plasmid pGBT-TopoIIIα in place of the plasmid pLex-TopoIIIα. The plasmid pGBT-TopoIIIα comprises the gene encoding human topoisomerase IIIα fused with the DNA-binding domain of GAL4.

The strain yCM17 was transformed with the plasmid isolated during the screening of the two-hybrid library and with the plasmid pGBT-TopoIIIα. Controls for specificity of interaction were also performed by transforming this strain with the control plasmids pGBT-HaRasVal12 or pGBT-Fe65, in place of the plasmid pGBT-TopoIIIα. A test of β-Gal activity on the cells transformed with the various plasmids was performed to demonstrate the protein-protein interactions.

The results of the test showed that only the yeasts transformed with the plasmid isolated during the screening of the two-hybrid library and with the plasmid pGBT-TopoIIIα exhibited a β-Gal+ activity, thus showing interaction between human topoisomerase IIIα and the C-terminal region of the polypeptides according to the invention. These results also show that this interaction is independent of the fusion protein used.

What is claimed is:

1. An isolated nucleic acid molecule comprising the nucleotide sequence of SEQ ID NO:3.

2. A vector comprising the isolated nucleic acid molecule of claim 1.

3. An expression vector comprising the isolated nucleic acid molecule of claim 1 under the control of a promoter.

4. A host cell transformed with the expression vector of claim 3.

5. A method for producing a polypeptide comprising the amino acid sequence of SEQ ID NO:4, comprising the steps of:

(a) culturing the host cell of claim 4 under conditions that permit production of the polypeptide; and (b) collecting the polypeptide from the culture, the host cell, or a combination thereof.

6. An isolated nucleic acid molecule that encodes a polypeptide comprising the amino acid sequence of SEQ ID NO:4.

7. A vector comprising the isolated nucleic acid molecule of claim 6.

8. An expression vector comprising the isolated nucleic acid molecule of claim 6 under the control of a promoter.

9. A host cell transformed with the expression vector of claim 8.

10. A method for producing an isolated polypeptide comprising the amino acid sequence of SEQ ID NO:4, comprising the steps of:

(a) culturing the host cell of claim 9 under conditions that permit production of the polypeptide; and (b) collecting the polypeptide from the culture, the host cell, or a combination thereof.

* * * * *

SEQUENCE LISTING

```
<160> NUMBER OF SEQ ID NOS: 15

<210> SEQ ID NO 1
<211> LENGTH: 2973
<212> TYPE: DNA
<213> ORGANISM: Homo sapiens

<400> SEQUENCE: 1

ggatccgagc tcgagatggc cctccgaggc gtgcggaaag tcctctgtgt ggccgaaaaa      60
```

-continued

```
aacgacgcgg ccaaggggat cgccgacctg ctgtcaaacg gtcgcatgag gcggagagaa    120
ggactttcaa aattcaacaa gatctatgaa tttgattatc atctgtatgg ccagaatgtt    180
accatggtaa tgacttcagt ttctggacat ttactggctc atgatttcca gatgcagttt    240
cgaaaatggc agagctgcaa ccctcttgtc ctctttgaag cagaaattga aaagtactgc    300
ccagagaatt ttgtagacat caagaaaact ttggaacgag agactcgcca gtgccaggct    360
ctggtgatct ggactgactg tgatagagaa ggcgaaaaca tcgggtttga gattatccac    420
gtgtgtaagg ctgtaaagcc caatctgcag gtgttgcgag cccgattctc tgagatcaca    480
ccccatgccg tcaggacagc ttgtgaaaac ctgaccgagc ctgatcagag ggtgagcgat    540
gctgtggatg tgaggcagga gctggacctg aggattggag ctgcctttac taggttccag    600
accctgcggc ttcagaggat tttcctgag gtgctggcag agcagctcat cagttacggc    660
agctgccagt tccccacact gggctttgtg gtggagcggt tcaaagccat tcaggctttt    720
gtaccagaaa tcttccacag aattaaagta actcatgacc acaaagatgg tatcgtagaa    780
ttcaactgga aaaggcatcg actctttaac cacacggctt gcctagttct ctatcagttg    840
tgtgtggagg atcccatggc aactgtggta gaggtcagat ctaagcccaa gagcaagtgg    900
cggcctcaag ccttggacac tgtggagctt gagaagctgg cttctcgaaa gttgagaata    960
aatgctaaag aaaccatgag gattgctgag aagctctaca ctcaagggta catcagctat   1020
ccccgaacag aaacaaacat tttcccaga gacttaaacc tgacggtgtt ggtggaacag   1080
cagacccccg atccacgctg gggggccttt gcccagagca ttctagagcg gggtggtccc   1140
accccacgca atgggaacaa gtctgaccaa gctcaccctc ccattcaccc caccaaatac   1200
accaacaact tacagggaga tgaacagcga ctgtacgagt ttattgttcg ccatttcctg   1260
gcttgctgct cccaggatgc tcaggggcag gagaccacag tggagatcga catcgctcag   1320
gaacgctttg tggcccatgg cctcatgatt ctggcccgaa actatctgga tgtgtatcca   1380
tatgatcact ggagtgacaa gatcctccct gtctatgagc aaggatccca ctttcagccc   1440
agcaccgtgg agatggtgga cggggagacc agcccaccca agctgctcac cgaggccgac   1500
ctcattgccc tcatggagaa gcatggcatt ggtacggatg ccactcatgc ggagcacatc   1560
gagaccatca aagcccggat gtacgtgggc ctcaccccag acaagcggtt cctccctggg   1620
cacctgggca tgggacttgt ggaaggttat gattccatgg gctatgaaat gtctaagcct   1680
gacctccggg ctgaactgga agctgatctg aagctgatct gtgatggcaa aaaggacaaa   1740
tttgtggttc taaggcagca agtgcagaaa tacaagcagg ttttcattga agcggtggct   1800
aaagcaaaga aattggacga ggccttggcc cagtactttg ggaatgggac agagttggcc   1860
cagcaagaag atatctaccc agccatgcca gagcccatca ggaagtgccc acagtgcaac   1920
aaggacatgg tccttaagac caagaagaat ggcgggttct acctcagctg catgggtttc   1980
ccagagtgtc gctcagctgt gtggcttcct gactcggtgc tggaggccag cagggacagc   2040
agtgtgtgtc cagtttgtca gccacaccct gtgtacaggt taaagttaaa gtttaagcgc   2100
ggtagccttc ccccgaccat gcctctggag tttgtttgct gcatcggcgg atgcgacgac   2160
accctgaggg agatcctgga cctgagattt tcaggggggcc cccccagggc tagccagccc   2220
tctggccgcc tgcaggctaa ccagtccctg aacaggatgg acaacagcca gcacccccag   2280
cctgctgaca gcagacagac tgggtcctca aaggctctgg cccagaccct cccaccaccc   2340
acggctgctg gtgaaagcaa ttctgtgacc tgcaactgtg gccaggaggc tgtgctgctc   2400
actgtccgta aggagggccc caaccggggc cggcagttct ttaagtgcaa cggaggtagc   2460
```

-continued

```
tgcaacttct tcctgtgggc agacagcccc aatccgggag caggagggcc tcctgccttg   2520

gcatatagac ccctgggcgc ctccctggga tgcccaccag gcccagggat ccacctaggt   2580

gggtttggca accctggtga tggcagtggt agtggcacat cctgcctttg cagccagccc   2640

tccgtcacac ggactgtgca gaaggatgga cccaacaagg ggcgccagtt ccacacatgt   2700

gccaagccga gagagcagca gtgtggcttt ttccagtggg tcgatgagaa caccgctcca   2760

gggacttctg gagccccgtc ctggacagga gacagaggaa gaaccctgga gtcggaagcc   2820

agaagcaaaa ggccccgggc cagttcctca gacatggggt ccacagcaaa gaaaccccgg   2880

aaatgcagcc tttgccacca gcctggacac acccgtccct tttgtcctca gaacagatga   2940

gctcagggta gggtagagaa gcttggagtc gac                                2973
```

```
<210> SEQ ID NO 2
<211> LENGTH: 974
<212> TYPE: PRT
<213> ORGANISM: Homo sapiens

<400> SEQUENCE: 2

Met Ala Leu Arg Gly Val Arg Lys Val Leu Cys Val Ala Glu Lys Asn
1               5                   10                  15

Asp Ala Ala Lys Gly Ile Ala Asp Leu Leu Ser Asn Gly Arg Met Arg
            20                  25                  30

Arg Arg Glu Gly Leu Ser Lys Phe Asn Lys Ile Tyr Glu Phe Asp Tyr
        35                  40                  45

His Leu Tyr Gly Gln Asn Val Thr Met Val Met Thr Ser Val Ser Gly
    50                  55                  60

His Leu Leu Ala His Asp Phe Gln Met Gln Phe Arg Lys Trp Gln Ser
65                  70                  75                  80

Cys Asn Pro Leu Val Leu Phe Glu Ala Glu Ile Glu Lys Tyr Cys Pro
                85                  90                  95

Glu Asn Phe Val Asp Ile Lys Lys Thr Leu Glu Arg Glu Thr Arg Gln
            100                 105                 110

Cys Gln Ala Leu Val Ile Trp Thr Asp Cys Asp Arg Glu Gly Glu Asn
        115                 120                 125

Ile Gly Phe Glu Ile Ile His Val Cys Lys Ala Val Lys Pro Asn Leu
    130                 135                 140

Gln Val Leu Arg Ala Arg Phe Ser Glu Ile Thr Pro His Ala Val Arg
145                 150                 155                 160

Thr Ala Cys Glu Asn Leu Thr Glu Pro Asp Gln Arg Val Ser Asp Ala
                165                 170                 175

Val Asp Val Arg Gln Glu Leu Asp Leu Arg Ile Gly Ala Ala Phe Thr
            180                 185                 190

Arg Phe Gln Thr Leu Arg Leu Gln Arg Ile Phe Pro Glu Val Leu Ala
        195                 200                 205

Glu Gln Leu Ile Ser Tyr Gly Ser Cys Gln Phe Pro Thr Leu Gly Phe
    210                 215                 220

Val Val Glu Arg Phe Lys Ala Ile Gln Ala Phe Val Pro Glu Ile Phe
225                 230                 235                 240

His Arg Ile Lys Val Thr His Asp His Lys Asp Gly Ile Val Glu Phe
                245                 250                 255

Asn Trp Lys Arg His Arg Leu Phe Asn His Thr Ala Cys Leu Val Leu
            260                 265                 270

Tyr Gln Leu Cys Val Glu Asp Pro Met Ala Thr Val Val Glu Val Arg
        275                 280                 285
```

-continued

```
Ser Lys Pro Lys Ser Lys Trp Arg Pro Gln Ala Leu Asp Thr Val Glu
    290                 295                 300

Leu Glu Lys Leu Ala Ser Arg Lys Leu Arg Ile Asn Ala Lys Glu Thr
305                 310                 315                 320

Met Arg Ile Ala Glu Lys Leu Tyr Thr Gln Gly Tyr Ile Ser Tyr Pro
                325                 330                 335

Arg Thr Glu Thr Asn Ile Phe Pro Arg Asp Leu Asn Leu Thr Val Leu
            340                 345                 350

Val Glu Gln Gln Thr Pro Asp Pro Arg Trp Gly Ala Phe Ala Gln Ser
        355                 360                 365

Ile Leu Glu Arg Gly Gly Pro Thr Pro Arg Asn Gly Asn Lys Ser Asp
    370                 375                 380

Gln Ala His Pro Pro Ile His Pro Thr Lys Tyr Thr Asn Asn Leu Gln
385                 390                 395                 400

Gly Asp Glu Gln Arg Leu Tyr Glu Phe Ile Val Arg His Phe Leu Ala
                405                 410                 415

Cys Cys Ser Gln Asp Ala Gln Gly Gln Glu Thr Thr Val Glu Ile Asp
            420                 425                 430

Ile Ala Gln Glu Arg Phe Val Ala His Gly Leu Met Ile Leu Ala Arg
        435                 440                 445

Asn Tyr Leu Asp Val Tyr Pro Tyr Asp His Trp Ser Asp Lys Ile Leu
    450                 455                 460

Pro Val Tyr Glu Gln Gly Ser His Phe Gln Pro Ser Thr Val Glu Met
465                 470                 475                 480

Val Asp Gly Glu Thr Ser Pro Pro Lys Leu Leu Thr Glu Ala Asp Leu
                485                 490                 495

Ile Ala Leu Met Glu Lys His Gly Ile Gly Thr Asp Ala Thr His Ala
            500                 505                 510

Glu His Ile Glu Thr Ile Lys Ala Arg Met Tyr Val Gly Leu Thr Pro
        515                 520                 525

Asp Lys Arg Phe Leu Pro Gly His Leu Gly Met Gly Leu Val Glu Gly
    530                 535                 540

Tyr Asp Ser Met Gly Tyr Glu Met Ser Lys Pro Asp Leu Arg Ala Glu
545                 550                 555                 560

Leu Glu Ala Asp Leu Lys Leu Ile Cys Asp Gly Lys Lys Asp Lys Phe
                565                 570                 575

Val Val Leu Arg Gln Gln Val Gln Lys Tyr Lys Gln Val Phe Ile Glu
            580                 585                 590

Ala Val Ala Lys Ala Lys Lys Leu Asp Glu Ala Leu Ala Gln Tyr Phe
        595                 600                 605

Gly Asn Gly Thr Glu Leu Ala Gln Gln Glu Asp Ile Tyr Pro Ala Met
    610                 615                 620

Pro Glu Pro Ile Arg Lys Cys Pro Gln Cys Asn Lys Asp Met Val Leu
625                 630                 635                 640

Lys Thr Lys Lys Asn Gly Gly Phe Tyr Leu Ser Cys Met Gly Phe Pro
                645                 650                 655

Glu Cys Arg Ser Ala Val Trp Leu Pro Asp Ser Val Leu Glu Ala Ser
            660                 665                 670

Arg Asp Ser Ser Val Cys Pro Val Cys Gln Pro His Pro Val Tyr Arg
        675                 680                 685

Leu Lys Leu Lys Phe Lys Arg Gly Ser Leu Pro Pro Thr Met Pro Leu
    690                 695                 700
```

-continued

```
Glu Phe Val Cys Cys Ile Gly Gly Cys Asp Asp Thr Leu Arg Glu Ile
705                 710                 715                 720

Leu Asp Leu Arg Phe Ser Gly Gly Pro Pro Arg Ala Ser Gln Pro Ser
                725                 730                 735

Gly Arg Leu Gln Ala Asn Gln Ser Leu Asn Arg Met Asp Asn Ser Gln
            740                 745                 750

His Pro Gln Pro Ala Asp Ser Arg Gln Thr Gly Ser Ser Lys Ala Leu
        755                 760                 765

Ala Gln Thr Leu Pro Pro Pro Thr Ala Ala Gly Glu Ser Asn Ser Val
    770                 775                 780

Thr Cys Asn Cys Gly Gln Glu Ala Val Leu Leu Thr Val Arg Lys Glu
785                 790                 795                 800

Gly Pro Asn Arg Gly Arg Gln Phe Phe Lys Cys Asn Gly Gly Ser Cys
                805                 810                 815

Asn Phe Phe Leu Trp Ala Asp Ser Pro Asn Pro Gly Ala Gly Gly Pro
            820                 825                 830

Pro Ala Leu Ala Tyr Arg Pro Leu Gly Ala Ser Leu Gly Cys Pro Pro
        835                 840                 845

Gly Pro Gly Ile His Leu Gly Gly Phe Gly Asn Pro Gly Asp Gly Ser
    850                 855                 860

Gly Ser Gly Thr Ser Cys Leu Cys Ser Gln Pro Ser Val Thr Arg Thr
865                 870                 875                 880

Val Gln Lys Asp Gly Pro Asn Lys Gly Arg Gln Phe His Thr Cys Ala
                885                 890                 895

Lys Pro Arg Glu Gln Gln Cys Gly Phe Phe Gln Trp Val Asp Glu Asn
            900                 905                 910

Thr Ala Pro Gly Thr Ser Gly Ala Pro Ser Trp Thr Gly Asp Arg Gly
        915                 920                 925

Arg Thr Leu Glu Ser Glu Ala Arg Ser Lys Arg Pro Arg Ala Ser Ser
    930                 935                 940

Ser Asp Met Gly Ser Thr Ala Lys Lys Pro Arg Lys Cys Ser Leu Cys
945                 950                 955                 960

His Gln Pro Gly His Thr Arg Pro Phe Cys Pro Gln Asn Arg
                965                 970
```

<210> SEQ ID NO 3
<211> LENGTH: 1233
<212> TYPE: DNA
<213> ORGANISM: Homo sapiens

<400> SEQUENCE: 3

```
catttgttag tagccactcc aggacgtcta gtggatatga tggaaagagg aaagattgga     60

ttagactttt gcaaatactt ggtgttagat gaagctgatc ggatgttgga tatggggttt    120

gagcctcaga ttcgtagaat agtcgaacaa gatactatgc ctccaaaggg tgtccgccac    180

actatgatgt ttagtgctac ttttcctaag gaaatacaga tgctggctcg tgatttctta    240

gatgaatata tcttcttggc tgtaggaaga gttggctcta cctctgaaaa catcacacag    300

aaagtagttt gggtggaaga atcagacaaa cggtcatttc tgcttgacct cctaaatgca    360

acaggcaagg attcactgac cttagtgttt gtggagacca aaaagggtgc agattctctg    420

gaggatttct tataccatga aggatacgca tgtaccagca tccatggaga ccgttctcag    480

agggatagag aagaggccct tcaccagttc cgctcaggaa aaagcccaat tttagtggct    540

acagcagtag cagcaagagg actggacatt tcaaatgtga aacatgttat caattttgac    600
```

-continued

```
ttgccaagtg atattgaaga atatgtacat cgtattggtc gtacgggacg tgtaggaaac    660

cttggcctgg caacctcatt ctttaacgag aggaacataa atattactaa ggatttgttg    720

gatcttcttg ttgaagctaa acaagaagtg ccgtcttggt tagaaaacat ggcttatgaa    780

caccactaca agggtagcag tcgtggacgt tctaagagca gatttagtgg agggtttggt    840

gccagagact accgacaaag tagcggtgcc agcagttcca gcttcagcag cagccgcgca    900

agcagcagcc gcagtggcgg aggtggccac ggtagcagca gaggatttgg tggaggtggc    960

tatggaggct tttacaacag tgatggatat ggaggaaatt ataactccca gggggttgac   1020

tggtggggta actgagcctg ctttgcagta ggtcaccctg ccaaacaagc taatatggaa   1080

accacatgta acttagccag actatacctt gtgtagcttc aagaactcgc agtacattac   1140

cagctgtgat tctccactga aatttttttt ttaagggagc tcaaggtcac aagaagaaat   1200

gaaaggaaca atcagcagcc ctgttcagaa gga                                1233
```

<210> SEQ ID NO 4
<211> LENGTH: 344
<212> TYPE: PRT
<213> ORGANISM: Homo sapiens

<400> SEQUENCE: 4

```
His Leu Leu Val Ala Thr Pro Gly Arg Leu Val Asp Met Met Glu Arg
1               5                   10                  15

Gly Lys Ile Gly Leu Asp Phe Cys Lys Tyr Leu Val Leu Asp Glu Ala
            20                  25                  30

Asp Arg Met Leu Asp Met Gly Phe Glu Pro Gln Ile Arg Arg Ile Val
        35                  40                  45

Glu Gln Asp Thr Met Pro Pro Lys Gly Val Arg His Thr Met Met Phe
    50                  55                  60

Ser Ala Thr Phe Pro Lys Glu Ile Gln Met Leu Ala Arg Asp Phe Leu
65                  70                  75                  80

Asp Glu Tyr Ile Phe Leu Ala Val Gly Arg Val Gly Ser Thr Ser Glu
                85                  90                  95

Asn Ile Thr Gln Lys Val Val Trp Val Glu Glu Ser Asp Lys Arg Ser
            100                 105                 110

Phe Leu Leu Asp Leu Leu Asn Ala Thr Gly Lys Asp Ser Leu Thr Leu
        115                 120                 125

Val Phe Val Glu Thr Lys Lys Gly Ala Asp Ser Leu Glu Asp Phe Leu
    130                 135                 140

Tyr His Glu Gly Tyr Ala Cys Thr Ser Ile His Gly Asp Arg Ser Gln
145                 150                 155                 160

Arg Asp Arg Glu Glu Ala Leu His Gln Phe Arg Ser Gly Lys Ser Pro
                165                 170                 175

Ile Leu Val Ala Thr Ala Val Ala Ala Arg Gly Leu Asp Ile Ser Asn
            180                 185                 190

Val Lys His Val Ile Asn Phe Asp Leu Pro Ser Asp Ile Glu Glu Tyr
        195                 200                 205

Val His Arg Ile Gly Arg Thr Gly Arg Val Gly Asn Leu Gly Leu Ala
    210                 215                 220

Thr Ser Phe Phe Asn Glu Arg Asn Ile Asn Ile Thr Lys Asp Leu Leu
225                 230                 235                 240

Asp Leu Leu Val Glu Ala Lys Gln Glu Val Pro Ser Trp Leu Glu Asn
                245                 250                 255
```

-continued

```
Met Ala Tyr Glu His His Tyr Lys Gly Ser Ser Arg Gly Arg Ser Lys
            260                 265                 270

Ser Arg Phe Ser Gly Gly Phe Gly Ala Arg Asp Tyr Arg Gln Ser Ser
        275                 280                 285

Gly Ala Ser Ser Ser Ser Phe Ser Ser Ser Arg Ala Ser Ser Ser Arg
    290                 295                 300

Ser Gly Gly Gly Gly His Gly Ser Ser Arg Gly Phe Gly Gly Gly Gly
305                 310                 315                 320

Tyr Gly Gly Phe Tyr Asn Ser Asp Gly Tyr Gly Gly Asn Tyr Asn Ser
                325                 330                 335

Gln Gly Val Asp Trp Trp Gly Asn
            340


<210> SEQ ID NO 5
<211> LENGTH: 5321
<212> TYPE: DNA
<213> ORGANISM: Homo sapiens

<400> SEQUENCE: 5

tttcccctta ctccgctccc ctcttttccc tccctctcct ccccttccct ctgttctctc      60

ctcctcttcc cctcccctcc cccgtccggg gcactctata ttcaagccac cgtttcctgc     120

ttcacaaaat ggccaccgca cgcgacacct acggtcacgt ggcctgccgc cctctcagtt     180

tcgggaatct gcctagctcc cactaagggg aggctacccg cggaagagcg agggcagatt     240

agaccggaga aatcccacca catctccaag cccgggaact gagagaggaa gaagagtgaa     300

ggccagtgtt aggaaaaaaa aaaacaaaaa caaaaaaaac gaaaaacgaa agctgagtgc     360

atagagttgg aaaggggagc gaatgcgtaa ggttggaaag gggggcgaag aggcctaggt     420

taacattttc aggcgtctta gccggtggaa agcgggagac gcaagttctc gcgagatctc     480

gagaactccg aggctgagac tagggtttta gcggagagca cgggaagtgt agctcgagag     540

aactgggaca gcatttcgca ccctaagctc caaggcagga ctgctagggg cgacaggact     600

aagtaggaaa tcccttgagc ttagacctga gggagcgcgc agtagccggg cagaagtcgc     660

cgcgacaggg aattgcggtg tgagagggag ggcacacgtt gtacgtgctg acgtagccgg     720

ctttccagcg ggtatattag atccgtggcc gcgcggtgcg ctccagagcc gcagttctcc     780

cgtgagaggg ccttcgcggt ggaacaaaca ctcgcttagc agcggaagac tccgagttct     840

cggtactctt cagggatgag tcatgtggca gtggaaaatg cgctcgggct ggaccagcag     900

tttgctggcc tagacctgaa ctcttcagat aatcagagtg gaggaagtac agccagcaaa     960

gggcgctata ttcctcctca tttaaggaac cgagaagcta ctagaggttt ctacgataaa    1020

gacagttcag ggtggagttc tagcaaagat aaggatgcgt atagcagttt tggatctcgt    1080

agtgattcaa gagggaagtc tagcttcttc agtgatcgtg gaagtggatc aaggggaagg    1140

tttgatgatc gtggacggag tgattacgat ggcattggca gccgtggtga cagaagtggc    1200

tttggcaaat ttgaacgtgg tggaaacagt cgctggtgtg acaaatcaga tgaagatgat    1260

tggtcaaaac cactcccacc aagtgaacgc ttggaacagg aactcttttc tggaggcaac    1320

actgggatta attttgagaa atacgatgac attccagttg aggcaacagg caacaactgt    1380

cctccacata ttgaaagttt cagtgatgtt gagatgggag aaattatcat gggaaacatt    1440

gagcttactc gttatactcg cccaactcca gtgcaaaagc atgctattcc tattatcaaa    1500

gagaaaagag acttgatggc ttgtgcccaa acagggtctg gaaaaactgc agcatttctg    1560

ttgcccatct tgagtcagat ttattcagat ggtccaggcg aggctttgag ggccatgaag    1620
```

-continued

```
gaaaatggaa ggtatgggcg ccgcaaacaa tacccaatct ccttggtatt agcaccaacg   1680
agagagttgg cagtacagat ctacgaagaa gccagaaaat tttcataccg atctagagtt   1740
cgtccttgcg tggtttatgg tggtgccgat attggtcagc agattcgaga cttggaacgt   1800
ggatgccatt tgttagtagc cactccagga cgtctagtgg atatgatgga aagaggaaag   1860
attggattag acttttgcaa atacttggtg ttagatgaag ctgatcggat gttggatatg   1920
gggtttgagc ctcagattcg tagaatagtc gaacaagata ctatgcctcc aaagggtgtc   1980
cgccacacta tgatgtttag tgctactttt cctaaggaaa tacagatgct ggctcgtgat   2040
ttcttagatg aatatatctt cttggctgta ggaagagttg gctctacctc tgaaaacatc   2100
acacagaaag tagtttgggt ggaagaatca gacaaacggt catttctgct tgacctccta   2160
aatgcaacag gcaaggattc actgacctta gtgtttgtgg agaccaaaaa gggtgcagat   2220
tctctggagg atttcttata ccatgaagga tacgcatgta ccagcatcca tggagaccgt   2280
tctcagaggg atagagaaga ggcccttcac cagttccgct caggaaaaag cccaatttta   2340
gtggctacag cagtagcagc aagaggactg gacatttcaa atgtgaaaca tgttatcaat   2400
tttgacttgc caagtgatat tgaagaatat gtacatcgta ttggtcgtac gggacgtgta   2460
ggaaaccttg gcctggcaac ctcattcttt aacgagagga acataaatat tactaaggat   2520
ttgttggatc ttcttgttga agctaaacaa gaagtgccgt cttggttaga aaacatggct   2580
tatgaacacc actacaaggg tagcagtcgt ggacgttcta agagtagcag atttagtgga   2640
gggtttggtg ccagagacta ccgacaaagt agcggtgcca gcagttccag cttcagcagc   2700
agccgcgcaa gcagcagccg cagtggcgga ggtggccacg gtagcagcag aggatttggt   2760
ggaggtggct atggaggctt ttacaacagt gatggatatg gaggaaatta taactcccag   2820
ggggttgact ggtggggtaa ctgagcctgc tttgcagtag gtcaccctgc caaacaagct   2880
aatatggaaa ccacatgtaa cttagccaga ctataccttg tgtagtttca agaactcgca   2940
gtacattacc agctgtgatt ctccactgaa atttttttt taagggagct caaggtcaca   3000
agaagaaatg aaaggaacaa tcagcagccc tgttcagaag gtggtttgaa gacttcattg   3060
ctgtagtttg gattaactcc cctcccgcct acccccatcc caaactgcat ttataatttt   3120
gtgactgagg atcatttgtt tgttaatgta ctgtgccttt aactatagac aactttttat   3180
tttgatgtcc tgttggctca gtaatgctca agatatcaat tgttttgaca aaataaattt   3240
actgaacttg gctaaaatc aaaccttggc acacaggtgt gatacaactt aacaggaatc    3300
atcgattcat ccataaataa tataaggaaa aacttatgcg gtagcctgca ttagggcttt   3360
ttgatacttg cagattgggg gaaaacaaca aatgtcttga agcatattaa tggaattagt   3420
ttctaatgtg gcaaactgta ttaagttaaa gttctgattt gctcactcta tcctggatag   3480
gtatttagaa cctgatagtc tttaagccat tccagtcatg atgaggtgat gtatgaatac   3540
atgcatacat tcaaagcact gttttcaaag ttaatgcaag taaatacagc aattcctctt   3600
tcaacgttta ggcagatcat taattatgag ctagccaaat gtgggcatac tattacaggg   3660
aaagtttaaa ggtctgataa cttgaaaata ggtttttagg agaattcatc tacttagact   3720
ttttaagtgc ctgccataaa tgaaattgaa atggtagaat ggctgaccac agcaatgacc   3780
agccctcatt agggccctgg atgatttttg gtctaataac gcatgctagt gttgatgttt   3840
tttggtcaga gggtatgaac aggaagaatt aaatgcagca ggctttattt taaatgccga   3900
ttcacattac tctgttcaag ctgcgttgag atgttaaact ggcttactat agacttcgta   3960
aaaatggctc cagaaaagta acaaactgaa atctttgaga tcacacaggt tggaaatatg   4020
```

-continued

```
tacataactg cacaaggtgt caattctgct ctacagtgca gttttagtca gttttagttg   4080

cataggtttc cattgtattt atagtctgtt tatgctaaat ctggccaaag atgaacattg   4140

tccaccacta aaatgcctct gccactttga attctgtgct aattttgtgg ccagaatgcg   4200

gtgatcaaaa cgctccatct ttttacagtg gcataggaag acggcaaaaa tttcctaaag   4260

tgcaatagat tttcaagtgt attgtgcctt gttctaaaac ttttattaag taggtgcact   4320

tgacagtatt gaggtcattt gttatggtgc tatttcaatt agtctaggtt taggcccttg   4380

tacattttgc ccataacttt ttacaaagta cttcttttat tgcacattca gagaatttta   4440

tatatatgtc ttgtgtgcgt gtccttaaac ttccaatctt actttgtctc ttggagattg   4500

ttgaacgcag cttgtctagg aaggggatgg gactagattc taaaatttat ttgggaccat   4560

gggaatgata gttgggaaga aaactatttg cacacgacag atttctagat actttttgct   4620

gctagcttta tgtaatattt attgaacatt ttgacaaata tttatttttg taagcctaaa   4680

agtgattctt tgaaagttta aagaaacttg accaaaagac agtacaaaaa cactggcact   4740

tgaatgttga atgtcaccgt atgcgtgaaa ttatatattt cggggtagtg tgagctttta   4800

atgtttaagt catattaaac tcttaagtca aattaagcag acccggcgtt ggcagtgtag   4860

ccataacttt ctgatgttag taaaaacaaa attggcgact tgaaattaaa ttatgccaag   4920

gttttgatac acttgtctta agatattaat gaaacacttc aaaacactga tgtgaagtgt   4980

ccagattctc agatgtttgt tgtgtggatt ttgtttagtt gtgtgttttt ttttttttca   5040

gtgaatgtct ggcacattgc aatcctcaaa catgtggtta tctttgttgt attggcataa   5100

tcagtgactt gtacattcag caatagcatt tgagcaagtt ttatcagcaa gcaatatttt   5160

cagttaataa ggtttcaaaa atcatgtaag gatttaaact tgctgaatgt aaagattgaa   5220

cctcaagtca ctgtagcttt agtaattgct tattgtatta gtttagatgc tagcactgca   5280

tgtgctgtgc atattctgat tttattaaaa taaaaaaaaa a                        5321


<210> SEQ ID NO 6
<211> LENGTH: 662
<212> TYPE: PRT
<213> ORGANISM: Homo sapiens

<400> SEQUENCE: 6

Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Arg Gly Phe Tyr Asp Lys Asp Ser Ser Gly Trp Ser Ser Ser Lys
    50                  55                  60

Asp Lys Asp Ala Tyr Ser Ser Phe Gly Ser Arg Ser Asp Ser Arg Gly
65                  70                  75                  80

Lys Ser Ser Phe Phe Ser Asp Arg Gly Ser Gly Ser Arg Gly Arg Phe
                85                  90                  95

Asp Asp Arg Gly Arg Ser Asp Tyr Asp Gly Ile Gly Ser Arg Gly Asp
            100                 105                 110

Arg Ser Gly Phe Gly Lys Phe Glu Arg Gly Gly Asn Ser Arg Trp Cys
        115                 120                 125

Asp Lys Ser Asp Glu Asp Asp Trp Ser Lys Pro Leu Pro Pro Ser Glu
    130                 135                 140
```

-continued

```
Arg Leu Glu Gln Glu Leu Phe Ser Gly Gly Asn Thr Gly Ile Asn Phe
145                 150                 155                 160

Glu Lys Tyr Asp Asp Ile Pro Val Glu Ala Thr Gly Asn Asn Cys Pro
                165                 170                 175

Pro His Ile Glu Ser Phe Ser Asp Val Glu Met Gly Glu Ile Ile Met
            180                 185                 190

Gly Asn Ile Glu Leu Thr Arg Tyr Thr Arg Pro Thr Pro Val Gln Lys
        195                 200                 205

His Ala Ile Pro Ile Ile Lys Glu Lys Arg Asp Leu Met Ala Cys Ala
    210                 215                 220

Gln Thr Gly Ser Gly Lys Thr Ala Ala Phe Leu Leu Pro Ile Leu Ser
225                 230                 235                 240

Gln Ile Tyr Ser Asp Gly Pro Gly Glu Ala Leu Arg Ala Met Lys Glu
                245                 250                 255

Asn Gly Arg Tyr Gly Arg Arg Lys Gln Tyr Pro Ile Ser Leu Val Leu
            260                 265                 270

Ala Pro Thr Arg Glu Leu Ala Val Gln Ile Tyr Glu Glu Ala Arg Lys
        275                 280                 285

Phe Ser Tyr Arg Ser Arg Val Arg Pro Cys Val Val Tyr Gly Gly Ala
    290                 295                 300

Asp Ile Gly Gln Gln Ile Arg Asp Leu Glu Arg Gly Cys His Leu Leu
305                 310                 315                 320

Val Ala Thr Pro Gly Arg Leu Val Asp Met Met Glu Arg Gly Lys Ile
                325                 330                 335

Gly Leu Asp Phe Cys Lys Tyr Leu Val Leu Asp Glu Ala Asp Arg Met
            340                 345                 350

Leu Asp Met Gly Phe Glu Pro Gln Ile Arg Arg Ile Val Glu Gln Asp
        355                 360                 365

Thr Met Pro Pro Lys Gly Val Arg His Thr Met Met Phe Ser Ala Thr
    370                 375                 380

Phe Pro Lys Glu Ile Gln Met Leu Ala Arg Asp Phe Leu Asp Glu Tyr
385                 390                 395                 400

Ile Phe Leu Ala Val Gly Arg Val Gly Ser Thr Ser Glu Asn Ile Thr
                405                 410                 415

Gln Lys Val Val Trp Val Glu Glu Ser Asp Lys Arg Ser Phe Leu Leu
            420                 425                 430

Asp Leu Leu Asn Ala Thr Gly Lys Asp Ser Leu Thr Leu Val Phe Val
        435                 440                 445

Glu Thr Lys Lys Gly Ala Asp Ser Leu Glu Asp Phe Leu Tyr His Glu
    450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
                485                 490                 495

Ala Thr Ala Val Ala Ala Arg Gly Leu Asp Ile Ser Asn Val Lys His
            500                 505                 510

Val Ile Asn Phe Asp Leu Pro Ser Asp Ile Glu Glu Tyr Val His Arg
        515                 520                 525

Ile Gly Arg Thr Gly Arg Val Gly Asn Leu Gly Leu Ala Thr Ser Phe
    530                 535                 540

Phe Asn Glu Arg Asn Ile Asn Ile Thr Lys Asp Leu Leu Asp Leu Leu
545                 550                 555                 560
```

-continued

```
Val Glu Ala Lys Gln Glu Val Pro Ser Trp Leu Glu Asn Met Ala Tyr
                565                 570                 575

Glu His His Tyr Lys Gly Ser Ser Arg Gly Arg Ser Lys Ser Ser Arg
            580                 585                 590

Phe Ser Gly Gly Phe Gly Ala Arg Asp Tyr Arg Gln Ser Ser Gly Ala
        595                 600                 605

Ser Ser Ser Ser Phe Ser Ser Ser Arg Ala Ser Ser Ser Arg Ser Gly
    610                 615                 620

Gly Gly Gly His Gly Ser Ser Arg Gly Phe Gly Gly Gly Gly Tyr Gly
625                 630                 635                 640

Gly Phe Tyr Asn Ser Asp Gly Tyr Gly Gly Asn Tyr Asn Ser Gln Gly
                645                 650                 655

Val Asp Trp Trp Gly Asn
            660


<210> SEQ ID NO 7
<211> LENGTH: 29
<212> TYPE: DNA
<213> ORGANISM: Artificial Sequence
<220> FEATURE:
<223> OTHER INFORMATION: oligonucleotide pGBT9(+2)

<400> SEQUENCE: 7

tcgccggaat tgaattcccg gggatccgt                                    29


<210> SEQ ID NO 8
<211> LENGTH: 24
<212> TYPE: DNA
<213> ORGANISM: Artificial Sequence
<220> FEATURE:
<223> OTHER INFORMATION: oligonucleotide pGBT9

<400> SEQUENCE: 8

tcgccggaat tcccggggat ccgt                                         24


<210> SEQ ID NO 9
<211> LENGTH: 20
<212> TYPE: DNA
<213> ORGANISM: Artificial Sequence
<220> FEATURE:
<223> OTHER INFORMATION: oligonucleotide 124

<400> SEQUENCE: 9

cgaggtctga ggatgatctt                                              20


<210> SEQ ID NO 10
<211> LENGTH: 20
<212> TYPE: DNA
<213> ORGANISM: Artificial Sequence
<220> FEATURE:
<223> OTHER INFORMATION: oligonucleotide 125

<400> SEQUENCE: 10

ctgagaaagt ggcgttctct                                              20


<210> SEQ ID NO 11
<211> LENGTH: 26
<212> TYPE: DNA
<213> ORGANISM: Artificial Sequence
<220> FEATURE:
<223> OTHER INFORMATION: oligonucleotide Top3XhoI
```

-continued

```
<400> SEQUENCE: 11

aagttactcg agatggccct ccgagg                                              26


<210> SEQ ID NO 12
<211> LENGTH: 27
<212> TYPE: DNA
<213> ORGANISM: Artificial Sequence
<220> FEATURE:
<223> OTHER INFORMATION: oligonucleotide Top3Hind3

<400> SEQUENCE: 12

acgagcaagc ttctctaccc taccctg                                             27


<210> SEQ ID NO 13
<211> LENGTH: 38
<212> TYPE: DNA
<213> ORGANISM: Artificial Sequence
<220> FEATURE:
<223> OTHER INFORMATION: oligonucleotide PCS1

<400> SEQUENCE: 13

aattgcgaat tctcgagccc ggggatccgt cgactgca                                 38


<210> SEQ ID NO 14
<211> LENGTH: 30
<212> TYPE: DNA
<213> ORGANISM: Artificial Sequence
<220> FEATURE:
<223> OTHER INFORMATION: oligonucleotide PCS2

<400> SEQUENCE: 14

gtcgcaggat ccccgggctc gagaattcgc                                          30


<210> SEQ ID NO 15
<211> LENGTH: 18
<212> TYPE: DNA
<213> ORGANISM: Artificial Sequence
<220> FEATURE:
<223> OTHER INFORMATION: oligonucleotide GALT4

<400> SEQUENCE: 15

ccactacaat ggatgatg                                                       18
```